United States Patent [19]

Lerk

[11] 4,244,941
[45] Jan. 13, 1981

[54] CONTROLLED RELEASE COMPOSITION AND PROCESS FOR PREPARING SAME

[75] Inventor: Coenraad F. Lerk, Roden, Netherlands

[73] Assignee: Gist-Brocades N.V., Delft, Netherlands

[21] Appl. No.: 624,734

[22] Filed: Oct. 23, 1975

Related U.S. Application Data

[63] Continuation of Ser. No. 404,601, Oct. 9, 1973, abandoned.

[30] Foreign Application Priority Data

Oct. 6, 1972 [GB] United Kingdom ............... 46299/72

[51] Int. Cl.³ .................... A01N 25/26; A61J 3/10; A61K 9/24; B05D 3/12
[52] U.S. Cl. .......................................... 424/21; 127/30; 252/1; 252/182; 252/316; 264/109; 424/33; 427/189; 427/190; 427/195; 427/221
[58] Field of Search ..................... 252/1, 316; 424/19, 424/33, 21; 427/189, 221, 190, 195

[56] References Cited

U.S. PATENT DOCUMENTS

| | | | |
|---|---|---|---|
| 3,096,248 | 7/1963 | Rudzki | 424/33 X |
| 3,259,482 | 7/1966 | Hansen | 427/212 X |
| 3,415,758 | 12/1968 | Powell et al. | 252/316 |
| 3,453,360 | 7/1969 | Hill | 424/33 X |
| 3,459,850 | 8/1969 | Riva | 424/19 X |
| 3,485,914 | 12/1969 | Corn | 424/22 |
| 3,577,514 | 5/1971 | Robinson | 424/22 |
| 3,732,172 | 5/1973 | Herbig et al. | 252/316 |

*Primary Examiner*—Richard D. Lovering
*Attorney, Agent, or Firm*—Hammond & Littell, Weissenberger and Muserlian

[57] ABSTRACT

Solid constant release composition wherein (a) the solution of soluble core substance within the core space remains saturated during dissolution and (b) the shape and (c) the surface of the coating and (d) the diffusion path for the soluble core substance through the porous coating remains constant while the composition is in a liquid medium, which composition is very useful in media in which constant release during substantially the whole release period is desired, for example, for medical, chemical and fermentation purposes.

16 Claims, 8 Drawing Figures

CONTROLLED RELEASE COMPOSITION AND PROCESS FOR PREPARING SAME

This is a continuation of Ser. No. 404,601, filed Oct. 9, 1973, and now abandoned.

STATE OF THE ART

Compositions comprising a core of a substance soluble in the liquid medium to which the composition is to be exposed, and, completely surrounding the core, a porous coating which is permeable to the liquid medium but is substantially insoluble, and does not disintegrate, in the medium, are known. For example, an oral tablet containing a medical agent as the soluble substance is disclosed in U.S. Pat. No. 3,538,214. The soluble substance in the tablet (prepared by methods known per se) is enveloped by a coating which forms a membrane in the liquid medium of the gastro-intestinal canal to which the tablet is exposed, and is slowly released. This slow release takes place through the action of the liquid in the gastro-intestinal canal passing through the membrane, dissolving the active substance of the core and passing again through the membrane so that the active substance is released in the gastro-intestinal canal. During the whole period of release, the coating remains substantially as it is, so that a slow, relatively uniform release of the active substance takes place, causing a prolonged action of the active substance. The coating around the core consists of a synthetic material such as cellulose acetate, ethyl cellulose or cellulose nitrate having a low permeability for water vapour, and optionally a plasticizer and dye. In addition, the coating should contain an auxiliary substance soluble in the liquid of the gastro-intestinal canal, so that after dissolution of this substance (which takes some time), the coating can act as a membrane. If it is desired that the active substance be released in the stomach, the auxiliary substance should be one which dissolves in the stomach under acid conditions; examples of which are calcium carbonate, polyvinylpyrrolidone and the higher molecular weight polyethyleneglycols. If, however, it is desired that the active substance be released in the intestinal canal, the auxiliary substance should dissolve in the basic medium of the intestinal canal, examples of which are benzoic, propionic or salicyclic acids. When manufacturing the coating, all components of the coating are mixed in a liquid, such as acetone or methyl alcohol, and then the mixture is sprayed on the tablet core by methods known per se, followed by removal of the liquid from the coating formed, e.g. by evaporation. Depending on the desired diffusion rate of the active substance from the core through the coating, the spraying process is continued for a period sufficient to obtain the required layer thickness.

Although the slow release of the active substance is assured, this tablet shows a release pattern which is not constant, i.e. the relationship between the percentage weight of the soluble active substance released in the surrounding liquid medium and the diffusion time is not linear.

In known coatings, such as discussed above, properties (a) to (d) are not all present at the same time. During transport of the liquid medium into the core, a saturated solution of the soluble core substance is not always formed in the core space, and the shape and surface of the coating in the liquid medium and the diffusion path for the soluble core substance through the coating do not always remain constant. In the above tablet of the U.S. Pat. No. 3,538,214, for instance, the shape and the surface of the coating in the liquid medium and the diffusion path for the soluble core substance through the coating do not remain constant, since the coating consists of a non-rigid plastic material and contains auxiliary substances which must dissolve in the liquid medium first, before the soluble core substance can be released. The auxiliary substances, however, are an essential part of the coating in order to prevent the coating being impermeable in the liquid medium, since otherwise the porosity would be lost. Only a saturated solution of core substance in the core space, in combination with a constant surface of a rigid coating and a constant diffusion path, will assure a constant release of soluble substance so that the release pattern of the soluble substance will be linear.

Another way of obtaining a sustained release of a soluble substance from a tablet is described in British Pat. No. 808,014, which describes a process of manufacturing tablets wherein a mixture of an insoluble resin and a soluble substance in powder form is tabletted. The tablets are not coated. The resin may be for example polyvinyl chloride, polyvinyl acetate and cellulose acetate or copolymers thereof.

When compressing the powder mixture under pressure, the resin forms a structurally stable non-porous matrix with pore-like channels containing the soluble substance in a compact form. When exposed to the liquid medium, the soluble substance is leached from these channels. After complete extraction of the soluble substance, the resin matrix remains. This matrix remains substantially intact or disintegrates slowly and uniformly, depending, for example, on the compression grade used during tabletting. The matrix structure remains intact until the soluble substance has been substantially all dissolved from the matrix.

The dissolution of the soluble substance may be represented by an exponential curve as shown in the British Patent since the dissolution rate is highest at the beginning of the dissolution, and decreases gradually. The diffusion path increases as the dissolution of the soluble substance advances, and the surface of the matrix changes by elution of the soluble substance leaving the pores. This means that there is no linear relationship between the percentage of soluble substance released to the surrounding liquid medium and the diffusion time.

The British Patent further discloses another embodiment consisting of preparing a core containing the soluble substance and coating the core with a mixture of resin and substance soluble in the liquid medium, the mixture being compressed in such a way that the resin forms a coherent, non-porous matrix structure, in which the soluble substance is again present in the channels of the pores. The core may be a normal tablet, but may also consist of a compressed mixture of resin and soluble substances, whereby the matrix formed regulates the dissolution pattern of the soluble core according to an exponential curve.

When the core is a normal tablet, and the dissolution rate is not influenced by other core components which may act as a matrix, one of the above requirements is fulfilled such as the shape of the coating remains unaltered in the liquid medium [requirement (b)]. However, the othe three requirements such as the saturation of the solution of soluble core substance within the core space during dissolution [requirement (a)], the surface of the coating in the liquid medium [requirement (c)] and the diffusion path of the soluble core substance through the coating [requirement (d)], which should remain unaltered, are not fulfilled. The coating of these tablets must, in order to guarantee the permeability for the liquid medium, contain substances soluble in this medium. Those substances may be the soluble core substances. In that case the dissolution pattern of the soluble substance from the coating is, as long as soluble substance is present therein, exponential since the diffusion path increases and the surface of the coating changes by leaching the soluble substance from the pores.

After the soluble substance has been leached from the coating, the soluble substance of the core dissolves. When the two soluble substances are the same, the dissolution pattern will be linear from then and only then will the four requirements be fulfilled simultaneously. When the soluble substance in the coating differs from that in the core, the soluble substance from the core is released only after the soluble substances have been leached from the coating, and again only from then will the dissolution pattern of the soluble core substance be linear. Before the soluble substance is leached from the coating, the soluble core substance has no diffusion path so that a saturated solution of soluble core substance cannot exist within the core space and thus once again the four requirements are not fulfilled simultaneously.

In both cases, the total dissolution pattern, counted from the moment the tablet is exposed to the liquid medium to the moment the soluble substance from the core is dissolved substantially completely, differ from linearity. Thus none of the known tablets described above fulfils the four requirements simultaneously.

OBJECTS OF THE INVENTION

It is an object of the invention to provide a novel composition for constant release of a soluble core substance.

It is another object of the invention to provide a novel process for the preparation of composition for constant release of a soluble core substance.

These and other objects and advantages of the invention will become obvious from the following detailed description.

THE INVENTION

The present invention provides a constant release composition wherein (a) the solution of soluble core substance within the core space remains saturated during dissolution, and (b) the shape and (c) the surface of the coating and (d) the diffusion path for the soluble core substance through the porous coating remains constant while the composition is in the liquid medium.

It has now been found that the four requirements to achieve a substantially constant release of the soluble substance in the liquid medium are fulfilled by a solid composition comprising a core of the soluble substance, and, completely surrounding the core, a rigid porous coating which is free or substantially free of substances which are soluble or swellable in the liquid medium. To prepare the compositions, the components of the coating are thoroughly dry mixed in the usual way, and the mixture so obtained is coated around the core, for instance, in a tabletting machine.

The release rate of the core substance from the composition is dependent upon the physico-chemical properties of both core and porous coating. While the four requirements are fulfilled during very nearly all of the diffusion period, as soon the amount of core substance is insufficient to support a saturated solution within the core space, i.e. just before the end of the diffusion process, the release of the core substance from the composition will in fact deviate from linearity.

It has been found that, in some cases, ageing of the composition during a few days, for example, 3 to 10 days, after the composition has been prepared in an atmosphere of a constant relative humidity of about 45 to 60%, preferably 50 to 55%, enhances the reproducibility of the releasing properties of the composition.

Suitable coating substances are substances insoluble in the medium in which they are intended to be used, and able to be compressed in powder form to an inert, non-disintegrating non-eroding porous coating. Suitable coating substances are, for example, polymers such as copolymers of vinyl chloride and vinyl acetate, or of vinylidene chloride and acrylonitrile, polyethylene, polymethylmethacrylate, polystyrene, inorganic substances such as dicalcium phosphate dihydrate, tricalcium phosphate and anhydrous calcium sulfate.

In some cases, it is advantageous to use one or more additives such as lubricants as usual for tabletting purposes and wetting agents especially for coating materials which have poor wetting properties in themselves.

Compression pressures to be applied on the coating material to surround the core substance and to attain the desired solidity depend on the circumstances and the materials used. As a general guidance, compression pressures of about 500 to 5000 kg/cm$^2$, preferably 800 to 2500 kg/cm$^2$ are suitable although in special cases different compression pressures are applied. Other circumstances which influence the final result are, for example, the coating weight, the tabletting pressure, the size of the powder particles. A higher coating weight generally results in a lower release rate; a higher tabletting pressure generally results also in a lower release rate, and a higher particle size tends to result in a higher release rate.

Effects of the liquid medium on the release rate are also very small, such as effects of motion of the medium, and pH of the medium. The pH of the medium will influence the release rate, of course, when the solubility of the soluble core substance varies with pH. Temperature effects are also small unless the solubility of the soluble core substance varies greatly with the temperature.

The composition of the invention can give a sustained constant or substantially constant delivery of the soluble substance present therein. Examples of the compositions are tablets containing a medicine for oral use. However, the scope of the invention is not restricted to dosage forms for oral use, but comprises also dosage forms for other ways of administration, e.g. tablets for implantation or vaginal tablets. A composition for anti-conception purposes is also an example. Further the invention includes, for example, tablets of reagents for chemical processes or analytical processes, or of physiologically active substances for microbiological processes.

In the following examples there are described several preferred embodiments to illustrate the invention. However, it should be understood that the invention is not intended to be limited to the specific embodiments.

EXAMPLE 1

Preparation of the Tablets 380 mg of crystalline potassium chloride were compressed in a rotary tablet machine under a pressure of 2600 kg using dies with a cross-section of 9 mm to give compressed potassium chloride cores. A copolymer of vinyl chloride and vinyl acetate having a particle size of 63 to 80 μm was mixed in a Planetary Mixer with 0.2% of magnesium lauryl sulfate as a lubricant. 300 mg of the resulting mixture was applied as a coating by a rotary tablet machine, which for this purpose was provided with accessories for tabletting a coating around a core, and dies having a cross-section of 13 mm. The coating was compressed under a pressure of 2900 kg. Sustained release tablets consisting of a potassium chloride core of a diameter of 9 mm surrounded by a coating of the copolymer having an overall diameter of 13 mm were obtained.

EXAMPLE 2

Relationship between the Release of the Active Substance and Time

Figure 1:
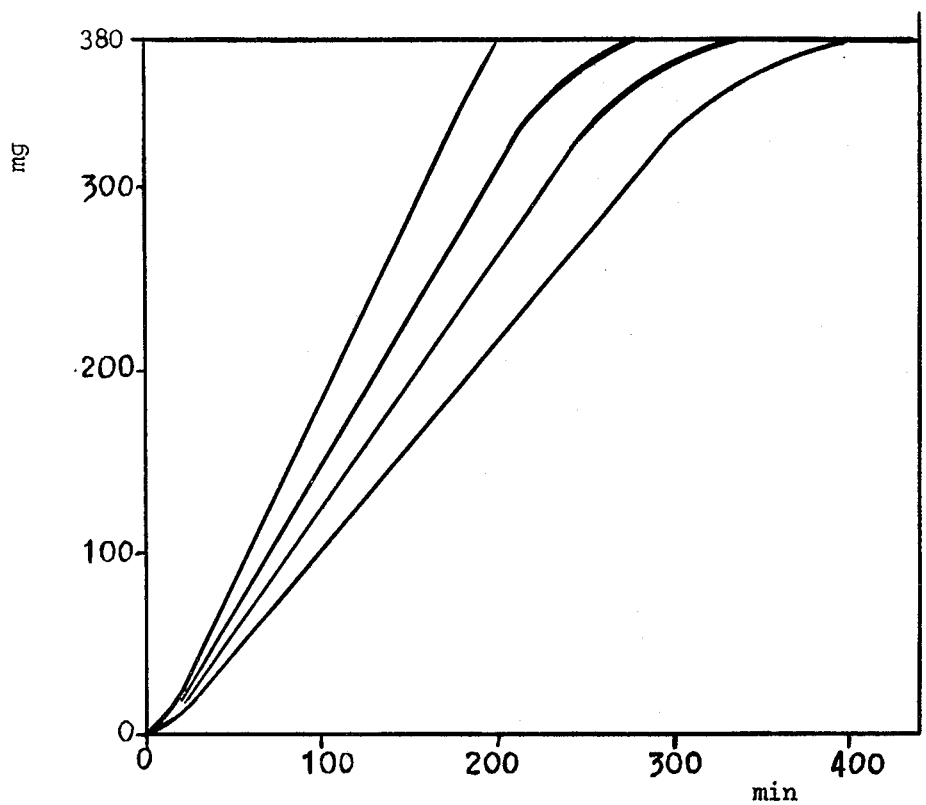
FIG. 1 shows the released KCl in mg plotted against the time in minutes for the tablets of Example 2 having a coating of a copolymer of vinyl chloride and vinyl acetate.
Figure 2:
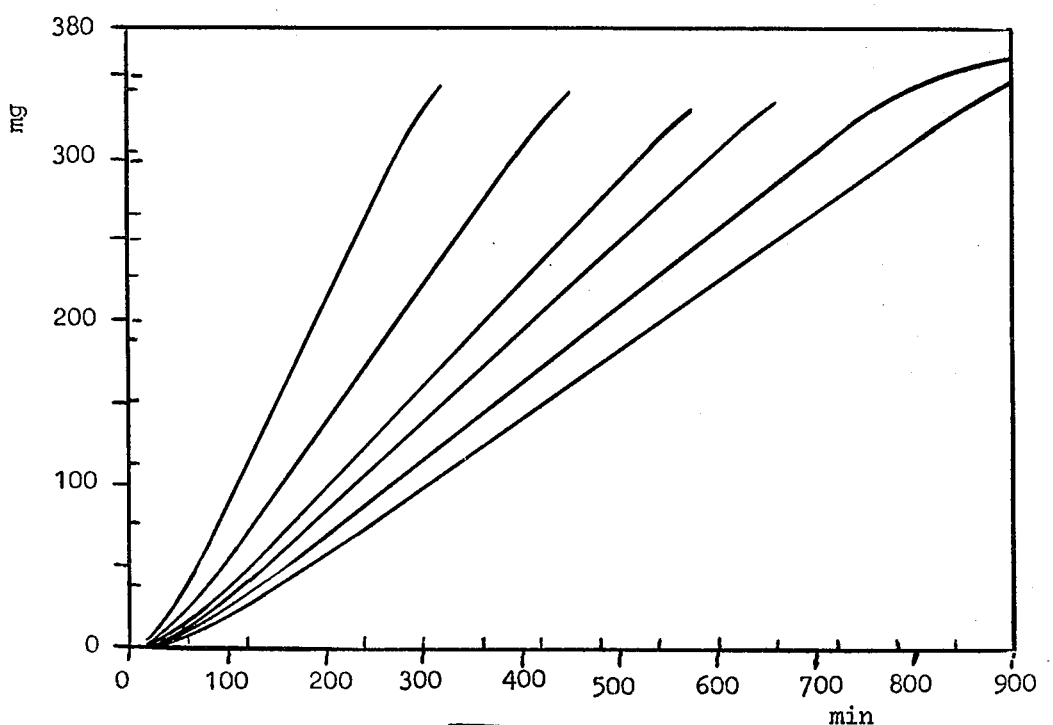
FIG. 2 shows the released KCl in mg plotted against the time in minutes for the tablets of Example 2 having a coating of a copolymer of vinylidene chloride and acrylonitrile.
Figure 3:
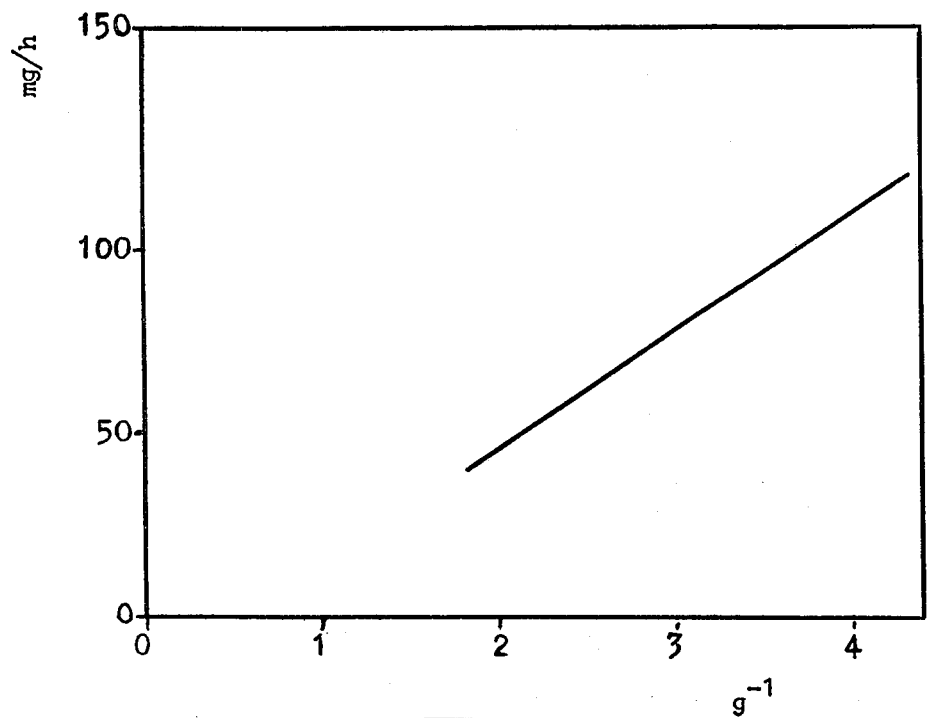
FIG. 3 shows the KCl flux in mg/hr plotted against the reciprocal coating weight in g for the tablets of Example 3.
Figure 4:
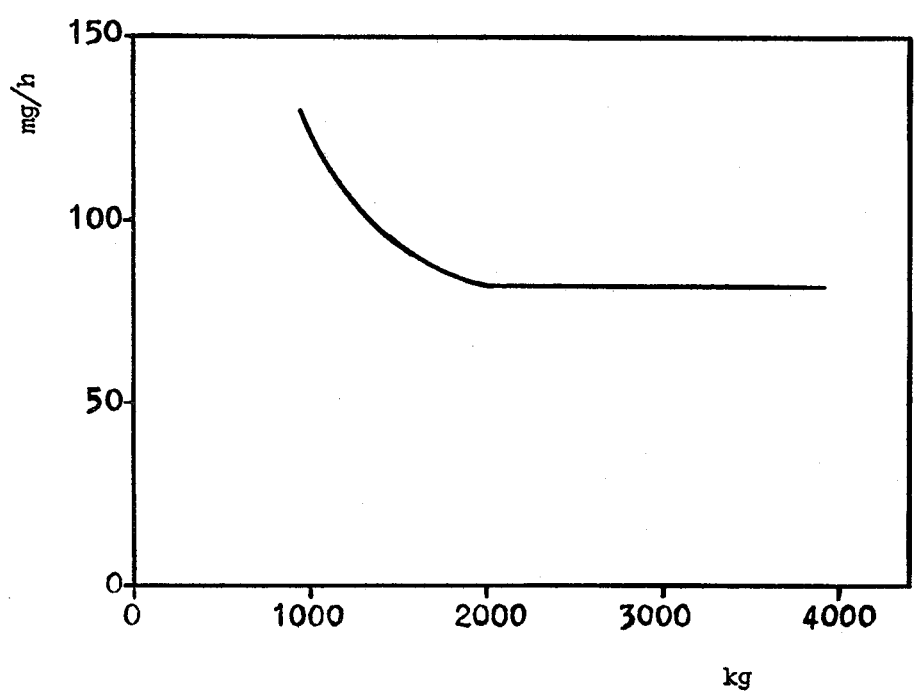
FIG. 4 shows the KCl flux in mg/hr plotted against the compression pressure for the coating for the tablets of Example 4.
Figure 5:
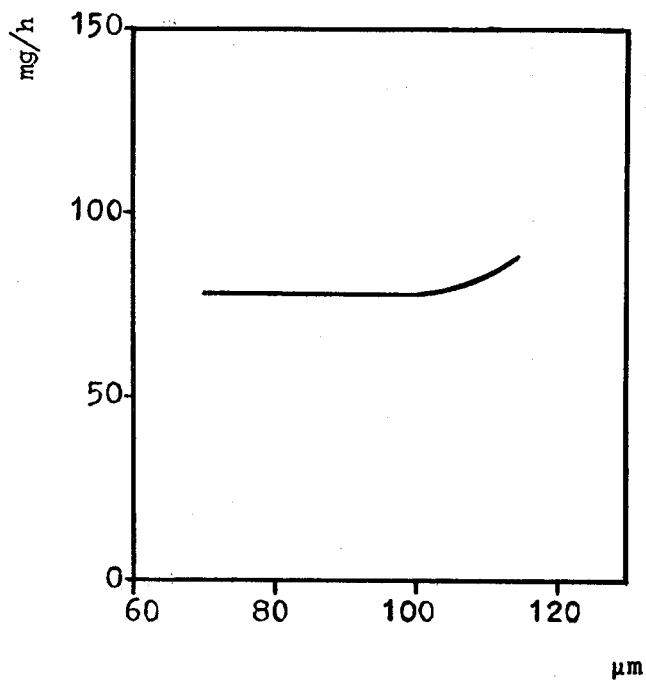
FIG. 5 shows the KCl flux in mg/hr plotted against the mean particle diameter of the polymer for the tablets of Example 5.
Figure 6:
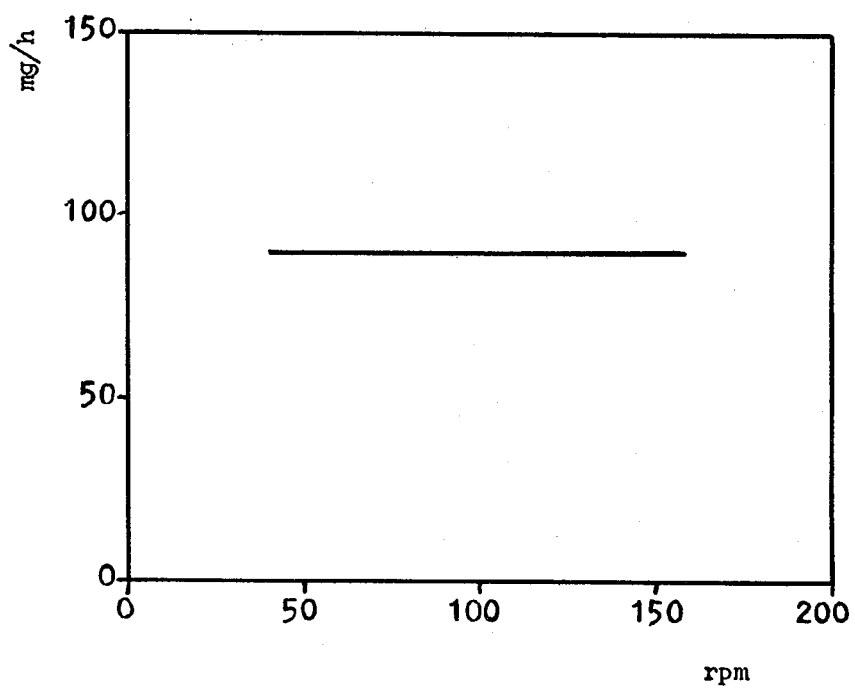
FIG. 6 shows the KCl flux in mg/hr plotted against the rotation speed of the basket in rpm for the tablets of Example 6.
Figure 7:
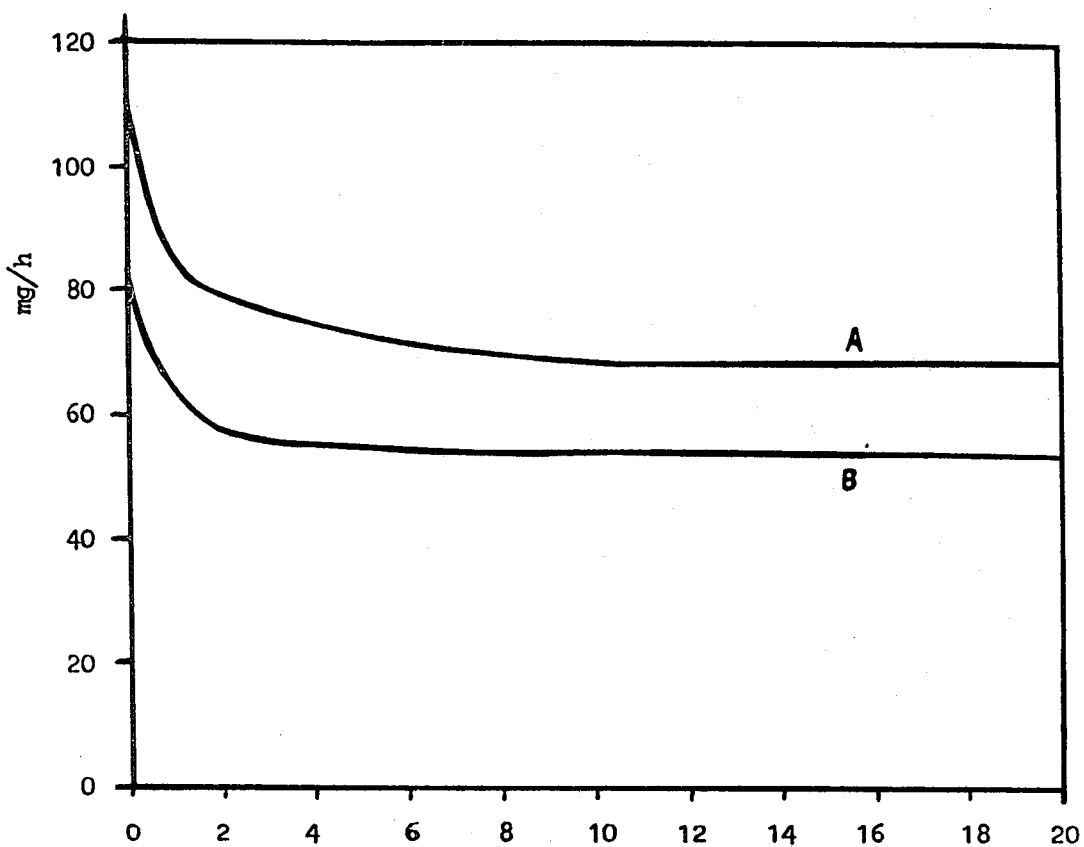
FIG. 7 shows the KCl flux in mg/hr plotted against the aging period in days for the tablets of Example 7.
Figure 8:
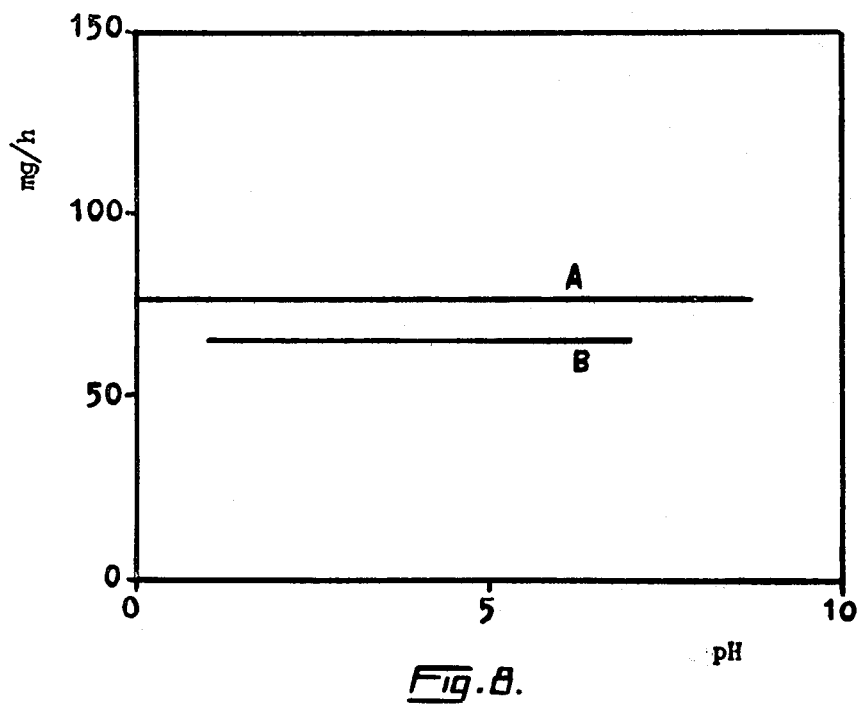
FIG. 8 shows the KCl flux in mg/hr plotted against the pH of the surrounding liquid for the tablets of Example 8.

A tablet core of 380 mg of potassium chloride was tabletted under a pressure of 2600 kg to give tablets of diameter 9 mm. A coating, consisting of a copolymer of vinyl chloride and vinyl acetate, was added using a compression pressure of 2900 kg to give tablets of diameter 13 mm. Several samples, in which the coating weight was 250, 300, 350 and 400 mg respectively were prepared with reciprocal amounts of lubricant. The release of the core substance was determined by the rotating basket method (USP XVIII), and the potassium chloride concentration was determined by conductivity measurements. The results are shown in FIG. 1 of the attached drawings, in which the released potassium chloride in mg is plotted against the time in minutes from the moment the tablet is contacted with the liquid. FIG. 1 shows straight curves from substantially the beginning to at least about the moment when 90% of the potassium chloride has been released from the tablet.

A similar experiment was carried out with a copolymer of vinylidene chloride and acrylonitrile as the coating substance. Samples in which the coating weight was 250, 300, 350, 400, 450 and 500 mg respectively were prepared. The result is shown in FIG. II.

EXAMPLE 3

Influence of Coating Weight on the Release Rate

In this example, the influence of the coating weight on the release rate of the active substance is shown for a tablet according to the invention. The core of the tablet consisted of 380 mg of potassium chloride tabletted under a pressure of 2600 kg and had a diameter of 9 mm. The coating consisted of a sieve fraction of a copolymer of vinyl chloride and vinyl acetate having a particle size of 63 to 80 μm. The coating was compressed under a pressure of 2900 kg and had a diameter of 13 mm. Several samples, in which the coating weight was 250, 300, 350, 400, 450 and 500 mg respectively, were prepared. The release rate was determined by the rotating basket method (USP XVIII) and the potassium chloride concentration was determined by conductivity measurements. The results are shown in FIG. III of the attached drawings. In FIG. III, the potassium chloride flux in mg/hr is plotted against the reciprocal coating weight in g, which should desirably result in a straight curve, since with this coating, the coating weight is nearly proportional to the coating thickness. FIG. III shows that the release rate plotted against the reciprocal coating weight results in the substantially straight curve.

EXAMPLE 4

Influence of the Tabletting Pressure on the Release Rate

The core of the tablet consisted of 380 mg of potassium chloride tabletted under a pressure of 2600 kg and had a diameter of 9 mm. The coating consisted of 300 mg of a sieve fraction of a copolymer of vinyl chloride and vinyl acetate having a particle size of 63 to 80 μm. The coating was compressed having varying pressures, i.e. 900, 1500, 2000, 2500, 3000, 3500 and 4000 kg. The diameter of the coating was 13 mm. The release rate was determined as in Example 3. The results are shown in FIG. IV of the attached drawings in which the potassium chloride flux in mg/hr in plotted against the compression pressure for the coating. FIG. IV shows that, the coating was compressed under a pressure of 2000 kg to 4000 kg, the pressure had substantially no influence on the release rate. Only with the low pressures was some influence observed.

EXAMPLE 5

Influence of the Particle Size on the Release Rate

The core of the tablet consisted of 380 mg of potassium chloride tabletted under a pressure of 2600 kg and had a diameter of 9 mm. The coating consisted of 300 mg of a sieve fraction of a copolymer of vinyl chloride and vinyl acetate having a mean particle diameter of 70, 85, 95 and 112 μm, respectively. The coating was compressed under a pressure of 2900 kg and the tablets had a diameter of 13 mm. The release rate was determined as in Example 3. The results are shown in FIG. V of the attached drawings, in which the potassium chloride flux in mg/hr is plotted against the mean particle diameter of the polymer. FIG. V shows that, in the region measured, the particle size of the coating had little influence on the release rate.

EXAMPLE 6

Influence of the Motion of the Surrounding Liquid on the Release Rate

The core of the tablet consisted of 380 mg of potassium chloride tabletted under a pressure of 2600 kg and had a diameter of 9 mm. The coating consisted of 300 mg of a sieve fraction of a copolymer of vinyl chloride and vinyl acetate having a particle size of 63 to 80 μm. The coating was compressed under a pressure of 2900 kg and had a diameter of 13 mm. The release rate was determined as in Example 3, with the difference that the basket, in which the tablet was placed, was rotated at varying speeds, i.e 50, 75, 100 and 150 rpm. The results are shown in FIG. VI in which the potassium chloride flux in mg/hr is plotted against the rotation speed of the basket in rpm.

FIG. VI shows that, the region measured, the motion of the liquid around the tablet has substantially no influence on the release rate; this is important in practice, when such a tablet is for instance orally administered since the difference in gastric and intestinal agitation as well as the individual differences will not influence the release rate.

EXAMPLE 7

Influence of Ageing of the Tablets

Tablets were prepared having a potassium chloride core as prepared according to Example 2, which was surrounded by either (A) 300 mg of a sieve fraction of a copolymer of vinyl chloride and vinyl acetate of a particle size of 63 to 80 μm or (B) as (A) but using a copolymer of vinylidene chloride and acrylontrile. The coating was compressed under a pressure of 2900 kg under the circumstances indicated in Example 2. The tablets were aged for different periods in an atmosphere having a relatively humidity of 52 to 54%, and the release rates were measured as indicated in Example 3. The results are shown in FIG. VII where the potassium chloride flux in mg/hr is plotted against the aging period in days. In both cases, a decrease in flux with the time is observed, but for tablets of type (A), a constant flux is observed after about 7 days, while for tablets of type (B) the constant release rate is observed after about 4 days.

EXAMPLE 8

Influence of the pH of the Surrounding Liquid on the Release Rate

The core of the tablet consisted of 380 mg of potassium chloride and the core was tabletted under a pressure of 2600 kg and had a diameter of 9 mm. The coating consisted of 300 mg of a sieve fraction of a copolymer of vinyl chloride and vinyl acetate having a particle size of 63 to 80 μm. The coating was compressed under a pressure of 2900 kg, and had a diameter of 13 mm. The release rate was determined as in Example 3, the liquid consisting of solutions having varying pH values. One experiment was carried out with 0.1 N hydrochloride acid (pH 1) and another experiment was carried out with the liquid having a pH of 3 (adjusted to that figure with a citric acid-phosphate buffered solution); a further experiment was carried out at pH 6.2, the liquid being distilled water (containing a trace of carbon dioxide), and still another experiment was carried out at pH 8 using a citric acid-phosphate buffered solution. The results are shown in FIG. VIII, in which the potassium chloride flux in mg/hr is plotted against the pH of the surrounding liquid, where curve A stands for tablets which were not aged, and curve B stands for tablets aged for 7 days in an atmosphere having a relative humidity of 52 to 54% FIG. VIII shows that the influence of the pH on the release rate of the tablet can be neglected. In this connection, it is appreciated, however, that the solubility of potassium chloride in solutions of varying pH is substantially the same. It may be expected that active substances having solubilities which vary according to the pH, or which are ionised in a different manner at varying pH values, would give different results.

EXAMPLE 9

Flux of Various Soluble Compounds and Various Coating Materials

Tablet cores of 240 mg of each of the soluble compounds indicated in the Table below, were tabletted to give tablets of a diameter of 9 mm. Coatings consisting of each of the coating materials indicated in the Table were added, using a compression pressure as indicated in the Table, to give tablets of diameter 13 mm. The constant release rate was determined by the rotating basket method as in Example 3. The results are shown in the last column of the Table.

TABLE

| Soluble Compound | Coating Material | Compression Pressure Coating Material (kg) | Flux (mg/hr) |
|---|---|---|---|
| 1. Orphenadrine HCl | | 1000 | 30 |
| 2. Ephedrine HCl | | 1000 | 29 |
| 3. Sodium pentobarbital | Copolymer of vinylidene | 1000 | 37 |
| 4. Procaine HCl | chloride and acrylo- | 1000 | 25 |
| 5. Potassium chloride | nitrile[1] | 1000 | 40 |
| 6. Potassium chloride[2] | | 1000 | 55 |
| 7. Sulfanilamide | | 1000 | 4.5 |
| 8. Orphenadrine HCl | | 2900 | 22 |
| 9. Ephedrine HCl | | 2900 | 39 |
| 10. Sodium pentobarbital | chloride and vinyl | 2900 | 20 |
| 11. Procaine HCl | acetate[3] | 2900 | 29 |
| 12. Potassium chloride[2] | | 2900 | 72 |
| 13. Ephedrine HCl | Polyethylenetere- | 2900 | 41 |
| 14. Sodium pentobarbital | | 2900 | 41 |

TABLE-continued

| Soluble Compound | Coating Material | Compression Pressure Coating Material (kg) | Flux (mg/hr) |
|---|---|---|---|
| 15. Potassium chloride[2] | phthalate[4] | 2900 | 53 |

[1] 400 mg, fraction 63–80 μm
[2] 385 mg core
[3] 300 mg, fraction 63–80 μm
[4] 400 mg, unfractionated, with 0.5% carboxypolymethylene

EXAMPLE 10

Preparation of a Glucose Tablet 556 mg of a mixture of glucose and 1% magnesium stearate were compressed in a rotary tablet machine under a pressure of 1400 kg to form a tablet having a cross-section of 12 mm. 1200 mg of a mixture of a copolymer of vinylidene chloride and acrylonitrile having a particle size of <330 μm and 1% of polytetrafluoroethylene were applied as a coating with a rotary tablet machine which, for this purpose, was provided with accessories for tabletting a coating around a core and dies having a cross-section of 16 mm. The coating was compressed under a pressure of 1000 kg, giving a sustained release tablet of a glucose core of a diameter of 12 mm surrounded by a coating of a copolymer having an overall diameter of 16 mm. The tablet, when brought into an aqueous medium, showed a release rate of glucose of 8.85 mg/hr, as estimated by the rotating basket method indicated in Example 3. Tablets of this kind are very useful for a constant release in fermentation media.

Various modifications of the composition and methods of the invention may be made without departing from the spirit or scope thereof and it is to be understood that the invention is to be limited only as defined in the appended claims.

I claim:

1. A constant release composition wherein (a) the solution of soluble core substance within the core space remains saturated during dissolution and (b) the shape and (c) the surface of the coating and (d) the diffusion path for the soluble core substance through the porous coating remain constant while the composition is in a liquid medium, comprising a core of the soluble substance and a rigid porous coating completely surrounding the core and which coating is substantially free of substances which are soluble or swellable in the liquid medium, said coating substance being selected from substances insoluble in the medium in which they are intended to be used and having been compressed in powder form to form an inert, non-disintegrating non-eroding porous coating.

2. A composition of claim 1 wherein the soluble core substance contains a medicament.

3. A composition of claim 1 wherein the soluble core substance contains a reagent for chemical processes.

4. A composition of claim 1 wherein the soluble core substance contains a physiologically active substance for microbiological processes.

5. A composition of claim 1 wherein the coating substance is a polymer selected from the group consisting of a copolymer of vinyl chloride and vinyl acetate, a copolymer of vinylidene chloride and acrylonitrile, polyethylene, polymethylmethacrylate and polystyrene.

6. A composition of claim 1 wherein the coating substance is an inorganic substance selected from the group consisting of dicalcium phosphate dihydrate, tricalcium phosphate and anhydrous calcium sulfate.

7. The composition of claim 1 wherein the soluble core substance is selected from the group consisting of potassium chloride, orphenadrine HCl, ephedrine HCl, sodium pentobarbital, procaine HCl, sulfanilamide and glucose.

8. A process for preparing a composition of claim 1 comprising dry mixing the components for the coating in the usual way, and coating the mixture so obtained completely around a core of soluble substance.

9. The process of claim 8 wherein the coating is applied in a tabletting machine.

10. The process of claim 8 wherein the coating is applied around the soluble core with a compression pressure of about 500 to 5000 kg/cm$^2$.

11. The process of claim 10 wherein the pressure is 800 to 2500 kg/cm$^2$.

12. The process of claim 8 wherein the soluble core substance contains a medicine.

13. The process of claim 8 wherein the soluble core substance contains a reagent for chemical processes.

14. The process of claim 8 wherein the soluble core substance contains a physiologically active substance for microbiological processes.

15. The process of claim 8 wherein the coating substance is a polymer selected from the group consisting of a copolymer of vinyl chloride and vinyl acetate, a copolymer of vinylidene chloride and acrylonitrile, polyethylene, polymethylmethacrylate and polystyrene.

16. The process of claim 8 wherein the coating substance is an inorganic substance selected from the group consisting of dicalcium phosphate dihydrate, tricalcium phosphate and anhydrous calcium sulfate.

* * * * *

UNITED STATES PATENT AND TRADEMARK OFFICE
CERTIFICATE OF CORRECTION

PATENT NO. : 4,244,941
DATED : January 13, 1981
INVENTOR(S) : COENRAAD F. LERK

It is certified that error appears in the above—identified patent and that said Letters Patent is hereby corrected as shown below:

Column 6, line 45: "in plotted" should read -- is plotted --.

Column 7, line 18: "the region" should read -- in the region --.

Column 8, line 14: "hydrochloride" should read

-- hydrochloric --.

Column 8, TABLE, under column "Coating Material, insert

-- Copolymer of --   before "chloride and vinyl acetate".

Column 9, line 25: "a copolymer" should read

-- the copolymer --.

Signed and Sealed this

Fourteenth Day of July 1981

[SEAL]

Attest:

GERALD J. MOSSINGHOFF

Attesting Officer    Commissioner of Patents and Trademarks